(12) United States Patent
Salsarulo et al.

(10) Patent No.: US 11,452,687 B2
(45) Date of Patent: Sep. 27, 2022

(54) ORAL MEDICAMENT COMPRISING AN OSMOTIC LAXATIVE INCORPORATED INTO A MATRIX BASED ON PLANT FATS WITH REDUCED DOSES OF MACROGOL

(71) Applicant: SALSARULO PHARMA, Boulogne-Billancourt (FR)

(72) Inventors: Gérard Salsarulo, Boulogne-Billancourt (FR); Gilles Salsarulo, Boulogne-Billancourt (FR)

(73) Assignee: SALSARULO PHARMA, Boulogne-Billancourt (FR)

( * ) Notice: Subject to any disclaimer, the term of this patent is extended or adjusted under 35 U.S.C. 154(b) by 52 days.

(21) Appl. No.: 16/467,249

(22) PCT Filed: Dec. 8, 2016

(86) PCT No.: PCT/FR2016/053270
§ 371 (c)(1),
(2) Date: Jun. 6, 2019

(87) PCT Pub. No.: WO2018/104591
PCT Pub. Date: Jun. 14, 2018

(65) Prior Publication Data
US 2020/0078293 A1     Mar. 12, 2020

(51) Int. Cl.
*A61K 9/00*       (2006.01)
*A61K 9/50*       (2006.01)
*A61K 31/765*     (2006.01)
*A61K 47/44*      (2017.01)

(52) U.S. Cl.
CPC .......... *A61K 9/0004* (2013.01); *A61K 9/5015* (2013.01); *A61K 31/765* (2013.01); *A61K 47/44* (2013.01)

(58) Field of Classification Search
None
See application file for complete search history.

(56) References Cited

U.S. PATENT DOCUMENTS

| 6,221,853 | B1 | 4/2001 | Salsarulo et al. | |
| 2007/0116728 | A1* | 5/2007 | Ioualalen | A61K 31/7048 424/400 |
| 2010/0221298 | A1 | 9/2010 | Ioualalen et al. | |

FOREIGN PATENT DOCUMENTS

| EP | 0 911 038 A1 | 4/1999 |
| FR | 2 852 843 A1 | 1/2004 |
| WO | 2013/044085 A1 | 3/2013 |

OTHER PUBLICATIONS

English translation of FR 2 852 843 (2020).*
English translation of Written Opinion for PCT/FR2016/053270 (dated 2020).*
Chapman et al. (Am J Gastroenterol 2013; 108:1508-1515).*
International Preliminary Report on Patentability dated Jun. 11, 2019, issued in corresponding International Application No. PCT/FR2016/053270, filed Dec. 8, 2016, 1 page.
International Search Report dated Jun. 30, 2017, issued in corresponding International Application No. PCT/FR2016/053270, filed Dec. 8, 2016, 7 pages.
Written Opinion of the International Searching Authority dated Jun. 30, 2017, issued in corresponding International Application No. PCT/FR2016/053270, filed Dec. 8, 2016, 7 pages.
Morris G., et al.,"Cochrane Review: Osmotic and stimulant laxatives for the management of childhood constipation (Review)" XP055273738, Evidence-based Child Health: A Cochrane Review Journal, vol. 8, No. 1, Jan. 2013, pp. 57-109.
Suporn T., et al.,"A randomised, double-blind study of polyethylene glycol 4000 and lactulose in the treatment of constipation in children" XP021190250, BMC Pediatrics, Biomed Central, London GB, vol. 14, No. 1, Jun. 2014, 9 pages.
Abut E., et al., "Administration of olive oil followed by a low volume of polyethylene glycol-electrolyte lavage solution improves patient satisfaction with right-side colonic cleansing over administration of the conventional volume of polyethylene glycol-electrolyte lavage solution for colonoscopy preparation" XP026494054, Gastrointestinal Endoscopy, Elsevier, NL, vol. 70, No. 3, Sep. 2009, pp. 515-521.

* cited by examiner

*Primary Examiner* — Patricia Duffy
*Assistant Examiner* — Garen Gotfredson
(74) *Attorney, Agent, or Firm* — Christensen O'Connor Johnson & Kindness PLLC

(57) ABSTRACT

Oral medicament comprising an osmotic laxative incorporated into a matrix based on plant fats. The present invention relates to an oral pharmaceutical composition comprising: between 30 and 55% by weight of said pharmaceutical composition of micronized anhydrous macrogol; and between 45 and 70% by weight of the pharmaceutical composition of a carrier consisting of an anhydrous hydrophobic lipid coating based on fatty compounds of plant origin, having a melting point of between 36 and 38° C., and to the use thereof as laxative. Said composition enables the reduction in the daily dosage of macrogol by preserving the osmotic pressure thereof as far as the colon, the site of therapeutic action of osmotic laxatives; said carrier protects the macrogol from a reduction, due to the moisture in the digestive tract, in the osmotic pressure.

5 Claims, No Drawings

ORAL MEDICAMENT COMPRISING AN OSMOTIC LAXATIVE INCORPORATED INTO A MATRIX BASED ON PLANT FATS WITH REDUCED DOSES OF MACROGOL

The present invention relates to the field of laxative pharmaceutical preparations based on macrogol (PEG); it enables a significant reduction of the daily dosage of macrogol, thereby reducing, and even eliminating the side effects resulting from an elevated daily dosage of this type of osmotic laxative.

The present invention is based on the incorporation of macrogol, also called PEG hereinafter, in a hydrophobic matrix based on plant fats with a melting point at the temperature of the human body, and more specifically ranging from 36° C. to 38° C., and the oral administration thereof (for example in the form of a gel or a paste).

Osmotic laxatives, such a macrogol, are part of a category of laxatives that retain water, increasing the volume of the stools, making them softer and easier to pass, and making it possible to treat the effects of constipation.

However, the operating principle of this type of laxative requires it to produce its effect in the colon (recognised site of therapeutic action of osmotic laxatives), i.e. it must maintain maximum osmotic pressure until it reaches the site of therapeutic action; consequently, an optimal formulation prevents the macrogol from coming into contact with the moisture in the digestive tract reducing the osmotic pressure, which forms the basis of the laxative efficacy of the macrogol, and only releases the macrogol when it has reached the colon.

A solution to this problem is disclosed in EP 0 911 038, which describes a formulation of lactulose, another osmotic laxative, in a coating carrier made of a mixture of paraffinic hydrocarbons and that is not of plant origin; this formulation reduces the doses of lactulose generally used, ranging from 10 to 30 g per day for an adult, down to 5 to 10 g per day for an adult, thereby reducing, and even eliminating the adverse effects of this type of ingredient (bloating, gas, stomach cramps) due to the administration of elevated doses of osmotic laxatives.

However, there is a bias against the medical use of paraffinic hydrocarbons, because of their origin.

Furthermore, these paraffinic compounds also have a lubricating effect on the bowel function and actively contribute to the laxative effect of the composition.

Various documents describe the use of macrogol:

For example, the International Application PCT WO 2013/044085 describes solid laxative compositions in the form of bars, chocolate bars for example, or sweets; the purpose of this type of formulation is to conceal the taste of the active ingredients. It should be noted that the formulations provided by way of example in this document comprise hydrophilic ingredients (salts, sucralose, milk powder present in white chocolate) and water, which make it impossible to maintain the anhydrous property of the macrogol until it reaches its site of therapeutic action; furthermore, there is nothing to indicate that the carrier of the disclosed formulations has a melting point ranging from 36 to 38° C.

Other publications, such as the clinical review study "Osmotic and stimulant laxatives for the management of childhood constipation" by Gordon et al. (A COCHRANE REVIEW JOURNAL, vol. 8, no 1, 1 Jan. 2013, p. 57-109), which compiles the data of various clinical trials of laxatives, or the article "A randomised, double-blind study of polyethylene glycol 4000 and lactulose in the treatment of constipation in children" by Treepongkaruna et al. BMC PEDIATRICS, BIOMED CENTRAL, LONDON, GB, vol. 14, no 1, 19 Jun. 2014, p. 153) which describes a study that compares the daily administration of 3.3 g of lactulose with that of 8 g of PEG for the treatment of constipation in children, propose the administration of reduced daily doses of macrogol. However, these are paediatric doses which, when adapted to the weight of the patient to be treated, correspond to conventional doses and cause negative side effects.

However, none of these documents proposes a galenic formulation of this laxative that is sufficiently efficacious to reduce the daily doses of administered macrogol.

The objective of the applicant is therefore to develop a laxative medicament for the treatment of constipation enabling reducing the daily doses of PEG, in order to reduce the side effects resulting from the administration of elevated doses of laxative, and the applicant has therefore developed a new galenic formulation of PEG based on plant compounds and non-paraffinic compounds:

which completely maintains the osmotic pressure of PEG, which is the basis of its laxative effect, until it reaches its site of therapeutic action, the colon;

which is not affected by the pH values inside the digestive tract;

which, surprisingly, enables the use of reduced PEG doses, ranging from 5 to 15 g/day, i.e. as low as in the case of a paraffinic carrier being used, and having as a consequence the significant reduction of unwanted side effects (stomach cramps, bloating, gas . . . );

of which the carrier is primarily of plant origin.

The Applicant produced this result by using, as carrier, an anhydrous hydrophobic lipid coating made of waxes and butters of plant origin, to which vegetable oils can be added, to achieve a melting point ranging from 36 to 38° C.; surprisingly, this carrier, which rests on a specific selection of excipients conventionally used for the formulation of medicaments, advantageously increases the efficacy of the macrogol and enables the administration of reduced doses of macrogol.

French Patent Application FR 2 852 843 discloses pharmaceutical formulations consisting of solid lipid particles obtained by means of a specific preparation method whereby lipid droplets are formed in a gel; in this application, there is no mention of trying to reduce the doses of active ingredient. This patent application relates to the development of a specific manufacturing process using lipid droplets and resulting in formulations that enable concealing the taste of the active ingredients; the Application therefore encompasses the use of a vast list of fatty excipients, including non-vegetable excipients. Furthermore, the preparation of these solid forms requires the use of a process that is more complex than that enabling the preparation of the pharmaceutical composition according the invention.

More specifically, the purpose of the oral pharmaceutical composition according to the invention is to maintain the osmotic pressure of the macrogol throughout its oral administration, inducing the reduction of the daily dosage of this laxative, and it comprises:

between 30 and 55% by weight of the pharmaceutical composition of anhydrous macrogol; the macrogol can be micronized, in this case the size of the particles is preferably between 75 and 150 µm; and between 45 and 70% by weight of the pharmaceutical composition of a carrier consisting of an anhydrous hydrophobic lipid coating based on fatty compound of plant origin; more specifically, this anhydrous hydrophobic lipid coating is made of:

*either up to 100% by weight of the carrier when it is shea butter and/or cocoa butter;

*or from 12 to 25%, preferably from 15 to 25%, by weight of the carrier of a vegetable wax;

and, depending on whether it is a vegetable butter or vegetable wax, from 25 to 88%, preferably from 25 to 85% by weight of the carrier of a vegetable oil allowing adjustment of the melting point of said carrier to 36 to 38° C.

The terms "osmotic and anhydrous laxative" is used to describe macrogol in powder form, containing less than 0.5% of water.

The fatty compounds of plant origin of the hydrophobic and anhydrous lipid carrier are chosen from a specific selection of products conventionally used by the person skilled in the field to produce hydrophobic coatings, within a given melting temperature range, such as carnauba wax, candelilla wax, rice bran wax, shea butter, cocoa butter or any other pharmaceutically-acceptable vegetable wax.

To reach a melting point of 36 to 38° C., some waxes and some butters require the addition of an anhydrous and hydrophobic vegetable oil such as sunflower oil, colza oil, corn oil, linseed oil or any mixture thereof.

If the objective is to improve the homogeneity of the composition according to the invention, the anhydrous and hydrophobic carrier can further comprise certain vegetable or non-vegetable compounds such as, for example glycerides and/or glycerol stearates.

The melting point of the anhydrous and hydrophobic lipid carrier can be conventionally measured to a variability of +/−5% by the implementation of a technique described in the applicable French Pharmacopeia or by a similar method.

The composition according to the invention is in the form of a paste or a gel to be administered orally.

To facilitate the administration of the composition according to the invention, the anhydrous and hydrophobic lipid carrier can comprise one or several aromas and/or sugar substitutes conventionally used in pharmaceutical compositions.

The anhydrous and hydrophobic carrier can also comprise an emulsifier such as glycerol stearates and cholesterol and/or a thinner, such as for example dimethicone (polydimethylsiloxane).

All the additional excipients used must be anhydrous in order to preserve the osmotic potential of the incorporated osmotic laxative.

The excipients of the composition are such that they do not comprise a cellulose derivative which would have the unwanted effect of absorbing the water present in the digestive tract, inducing a reduction of the osmotic pressure of the macrogol.

According to a particular embodiment of the present invention, the oral pharmaceutical composition is made of:
between 30 and 55% by weight of the pharmaceutical composition of anhydrous macrogol; the macrogol can be micronized, in this case the size of the particles is preferably between 75 and 150 μm; and
between 45 and 70% by weight of the pharmaceutical composition of a carrier consisting of an anhydrous hydrophobic lipid coating based on fatty compound of plant origin; more specifically, this anhydrous hydrophobic lipid coating is made of:
*either up to 100% by weight of the carrier when it is shea butter and/or cocoa butter;
*or from 12 to 25%, preferably from 15 to 25%, by weight of the carrier of a vegetable wax; and, depending on whether it is a vegetable butter or vegetable wax, from 25 to 88%, preferably from 25 to 85% by weight of the carrier of a vegetable oil allowing adjustment of the melting point of said carrier to 36 to 38° C.;

between 0 and 5% by weight of the pharmaceutical composition of an excipient selected from thinners, agents that improve the homogeneity of the composition, aromas, sugar substitutes and/or emulsifiers.

The Applicant was able to demonstrate that, when the oral pharmaceutical composition according to the invention is administered, the lipid anhydrous and hydrophobic carrier surrounds and protects the macrogol from the moisture of the digestive tract; until it reaches the colon, the macrogol retains an osmotic pressure close to its initial pressure, thereby reducing the daily dosage. It should be noted that the colon is the conventionally-recognised site of therapeutic action of osmotic laxative.

The ratio of anhydrous and hydrophobic lipid coating to active ingredient is adapted to withstand the duration of a gastric cycle in order to achieve optimal breakdown and the release of the macrogol in the colon, without the macrogol coming into direct contact with the moisture of the digestive tract, which would cause a reduction of the osmotic pressure before reaching the colon.

The present invention relates advantageously to a use of the composition according to the invention as a laxative, in particular for the treatment of constipation, preferably among adults; with this optimised formulation, this use is such that the macrogol is administered in a quantity representing reduced daily dosages, of between 5 to 15 g per day for an adult, contrary to existing medicaments based on macrogol, the daily dosage of which varies between 10 and 30 g per day.

According to a specific embodiment, the carrier is made of a vegetable wax to which a vegetable oil is added; the oral pharmaceutical composition according to the invention is then made of:

| | |
|---|---|
| Active ingredient: macrogol | from 45.00 to 55.00 g |
| Excipient: | |
| Vegetable wax | from 6.00 to 11.00 g, preferably from 9.00 to 11.00 g |
| Vegetable oil | from 32.00 to 37.00 g |
| Optionally, an agent to improve homogeneity | from 1.80 to 1.90 g |
| Other excipients such as thinner, emulsifier, aromas and/or sweeteners | from 1.60 to 1.80 g |

According to a more specific embodiment, the oral pharmaceutical composition according to the invention is made of:

| | |
|---|---|
| Active ingredient: macrogol | from 45.00 to 55.00 g |
| Excipient: | |
| Carnauba wax | from 6.00 to 11.00 g, preferably from 9.00 to 11.00 g |
| Corn oil | from 32.00 to 37.00 g |
| Optionally glycerol stearate | from 1.80 to 1.90 g |
| Other excipients such as thinner, emulsifier, aromas and/or sweeteners | from 1.60 to 1.80 g |

The macrogol can be a micronized or a non-micronized macrogol, of type 4000 or 3350.

This type of composition is prepared by first mixing the vegetable wax and the vegetable oil in a bath heated to approximately 90° C.; the mixture is then cooled to approximately 75° C. and the glycerol stearate can be added; then the other excipients are added; the mixture is stirred until obtaining a homogeneous mixture; the mixture is cooled to approximately 45° C. and the active ingredient is added to the mixture.

According to another specific embodiment, the carrier is made of a vegetable butter, and possibly vegetable oil; the oral pharmaceutical composition according to the invention is then made of:

| | |
|---|---|
| Active ingredient: macrogol | from 35.00 to 50.00 g, preferably from 35.00 to 45.00 g |
| Excipients: | |
| Vegetable butter (shea and/or cocoa) | from 55.00 to 65.00 g |
| Other excipients such as thinner, emulsifier, aromas and/or sweeteners | from 2.00 to 5.00 g, preferably from 2.00 to 4.00 g |

According to another embodiment, the oral pharmaceutical composition according to the invention is made of:

| | |
|---|---|
| Active ingredient: micronized macrogol | from 35.00 to 45.00 g |
| Excipients: | |
| Vegetable butter (shea and/or cocoa) | from 30.00 to 50.00 g |
| Vegetable oil | from 15.00 to 25.00 g |
| Other excipients such as thinner, emulsifier, aromas and/or sweeteners | from 2.00 to 5.00 g |

According to yet another embodiment, the oral pharmaceutical composition according to the invention is made of:

| | |
|---|---|
| Active ingredient: macrogol | from 35.00 to 45.00 g |
| Excipients: | |
| Shea butter | from 30.00 to 50.00 g |
| Cocoa butter | from 3.00 to 10.00 g |
| Corn oil | from 15.00 to 25.00 g |
| Other excipients such as thinner, emulsifier, aromas and/or sweeteners | from 2.00 to 5.00 g, preferably from 2.00 to 4.00 g |

The macrogol can be a micronized or a non-micronized macrogol, of type 4000 or 3350.

This type of composition is prepared by melting the vegetable butter or butters at a temperature between 45 and 50° C., followed by the addition of oil, and by the addition of the micronized ingredient and any other excipients, and by stirring of the mixture.

The present invention also relates to the use of an anhydrous and hydrophobic carrier with a melting point ranging from 36 to 38° C., made of fatty compounds of plant origin with a melting point ranging from 36 to 38° C. such as defined above and, optionally, up to 5% by weight of an excipient selected among thinners, agents improving homogeneity, emulsifiers, aromas and/or sweeteners; to preserve the osmotic pressure of the macrogol to the colon. The term "preserve the osmotic pressure of the macrogol" describes maintaining the macrogol in anhydrous form (water content of less than 0.5%) until it reaches the colon, this objective being achieved by means of the anhydrous and hydrophobic lipid carrier that prevents the macrogol from coming into contact with the moisture of the digestive tract, which reduces its osmotic pressure, which induces the reduction of the dosage of the macrogol in the composition according to the invention.

EXAMPLES

Examples of Compositions According to the Invention

Composition 1A

| | |
|---|---|
| Active ingredient: micronized macrogol 4000 | 50.00 g |
| Excipient: | |
| Carnauba wax | 9.65 g |
| Corn oil | 36.70 g |
| Gylcerol stearate | 1.87 g |
| Other excipients (Cholesterol, aroma, aspartame) | 1.78 g |

Composition 1B

| | |
|---|---|
| Active ingredient: micronized macrogol 4000 | 50.00 g |
| Excipient: | |
| Carnauba wax | 6.20 g |
| Corn oil | 38.70 g |
| Gylcerol stearate | 1.87 g |
| Other excipients (Cholesterol, aroma, aspartame) | 3.23 g |

Composition 2A

| | |
|---|---|
| Active ingredient: macrogol 3350 | 55.00 g |
| Excipients: | |
| Carnauba wax | 9.35 g |
| Sunflower oil | 33.87 g |
| Other excipients (Aromas, emulsifier, sweetener) | 1.78 g |

Composition 3A

| | |
|---|---|
| Active ingredient: micronized macrogol 4000 | 35.00 g |
| Excipients: | |
| Shea butter | 62.00 g |
| Other excipients (Aromas, emulsifier, sweetener, thinner) | 3.00 g |

Composition 3B

| | |
|---|---|
| Active ingredient: micronized macrogol 4000 | 40.00 g |
| Excipients: | |
| Shea butter | 35.00 g |
| Cocoa butter | 5.00 g |
| Corn oil | 17.00 g |
| Other excipients (Aromas, emulsifier, sweetener, thinner) | 3.00 g |

The invention claimed is:

1. A method of treatment of constipation in an adult comprising administering an effective amount of an oral pharmaceutical composition as a laxative to an adult in need thereof, wherein said composition is administered in a quantity featuring a reduced dosage of macrogol of 5 g to 15 g per day, wherein the oral pharmaceutical composition comprises:

from 30% to 55% by weight of the oral pharmaceutical composition of anhydrous macrogol, the anhydrous macrogol being in the form of a powder;

from 45% to 70% by weight of the oral pharmaceutical composition of a carrier consisting of an anhydrous hydrophobic lipid coating surrounding the anhydrous macrogol, the anhydrous hydrophobic lipid coating comprising a fatty compound of plant origin and with a melting point between 36 and 38° C.; and from 0% to 5% by weight of the oral pharmaceutical composition of an excipient selected from the group consisting of thinners, agents that improve homogeneity, sweeteners, aromas, emulsifiers, and combinations thereof, wherein a ratio of a first weight fraction of the anhydrous hydrophobic lipid coating between 45% and 70% of the composition to a second weight fraction of the macrogol between 30% and 55% of the composition is selected such that the anhydrous hydrophobic lipid coating maintains the osmotic pressure of the reduced dosage of the anhydrous macrogol until the oral pharmaceutical composition reaches the colon, thereby localizing administration at the colon.

2. The method of claim 1, wherein the reduced dosage, released in the colon, reduces unwanted side effects selected from stomach cramps, bloating and flatulence.

3. The method of claim 1, wherein the oral pharmaceutical composition localizes the treatment of constipation to the colon, as a result of the oral pharmaceutical composition affording osmotic protection until the pharmaceutical composition reaches the colon.

4. The method of claim 1, wherein the anhydrous hydrophobic lipid coating of said oral pharmaceutical composition comprises:

up to 100% by weight of the carrier of shea butter, cocoa butter, or a combination thereof; or from 12% to 25% by weight of the carrier of vegetable wax; and from 25% to 88% by weight of the carrier of a vegetable oil, to a sum total of 100%, providing the melting point of said carrier between 36° C. to 38° C.

5. The method of claim 4, wherein the vegetable oil is selected from the group consisting of sunflower oil, colza oil, corn oil, linseed oil, and a mixture thereof.

* * * * *